United States Patent [19]

Hayakawa et al.

[11] Patent Number: 5,661,034
[45] Date of Patent: Aug. 26, 1997

[54] SERUM-FREE MEDIUM FOR TISSUE CULTURE CONTAINING TISSUE INHIBITOR OF METALLOPROTEINASES AND METHOD FOR GROWING CELLS USING THE MEDIUM

[75] Inventors: Taro Hayakawa; Kyoko Yamashita, both of Nagoya; Kazushi Iwata, Takaoka, all of Japan

[73] Assignee: Fuji Yakuhin Kogyo Kabushiki Kaisha, Toyama-ken, Japan

[21] Appl. No.: 342,029

[22] Filed: Nov. 16, 1994

Related U.S. Application Data

[63] Continuation of Ser. No. 987,283, Mar. 16, 1993, abandoned.

[30] Foreign Application Priority Data

Jul. 18, 1991 [JP] Japan .................................. 3-268134

[51] Int. Cl.$^6$ ...................................................... C12N 5/00
[52] U.S. Cl. ........................... 435/383; 435/347; 435/373; 435/384
[58] Field of Search ........................... 435/240.2, 240.21, 435/240.23, 240.3, 240.31

[56] References Cited

FOREIGN PATENT DOCUMENTS

| | | |
|---|---|---|
| 61-282095 | 12/1986 | Japan . |
| 2-171182 | 7/1990 | Japan . |
| 2169295 | 7/1986 | United Kingdom . |

OTHER PUBLICATIONS

Hayakawa et al, FEBS Letters, 268(1), Jul. 30, 1990, pp. 125–128. (Biosis Abstract).
Docherty et al, Nature (London), 318 (6041), 1985, pp. 66–69. (Biosis Abstract).
Bertaux et al, Pathologie Biologie, 38(10), 1990, pp. 1029–1033 (Biosis Abstract).
Mather et al, "Mammalian Cell Culture", 1984, Chapter 2, pp. 17–52.
Welgus et al., J. Biol. Chem (1983) 258:12259–12264.
Umenishi, et al., J. Biochem, (1991) 110(2):189–195.
Westbrook, et al., Journal of Biol. Chem (1984) 259(16):9992–9996.
Kodama, et al. Matrix (1989) 9:1–6.
Hayashi, et al. Nature (1976) 259:132–134.
Lee et al. Nature (1981) 294:228–232.
Avalos, et al., Blood (1988) 71(6):1720–1725.
Gasson, et al. Nature (1985) 315:768–771.
Stanley, et al., EMBO J. (1984) 3:1429–1434.
Gewert, et al. EMBO J. (1987) 6:651–657.
Edwards et al. Nucleic Acid Res. (1986) 14:8863–8878.
Kodama, et al., Collagen Rel. Res. (1987) 7:341–350.
Hinegardner, Anal. Biochem. (1971) 39:197–201.
Kodama, et al., J. Immunol. Meth. (1990) 127: 103–108.
Marsh et al., Gene (1984) 32:481–485.
Okabe et al., Cancer RES. (1986) 46:1043–1046.
Golde, et al., Proc. Natl. Acad. Sci USA (1980) 77(1):593–596.
ATCC Catalogue of Cell Lines & Hybridomas, 6th edition, pp. 342–355 (1988).
Bjare et al, Pharmac. Ther., 53 (3), pp. 355–374 (1992).
Barnes et al, Analytical Biochemistry, vol. 102, pp. 255–270 (1980).

*Primary Examiner*—Michael G. Wityshyn
*Assistant Examiner*—Kristin Larson
*Attorney, Agent, or Firm*—Birch, Stewart, Kolasch & Birch, LLP

[57] ABSTRACT

Provided are serum-free media for tissue culture containing tissue inhibitor of metalloproteinases and methods for culturing animal cells using these media.

6 Claims, 9 Drawing Sheets

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear     ( i i ) MOLECULE TYPE: other nucleic acid     ( i i i ) HYPOTHETICAL: NO     ( x i ) SEQUENCE DESCRIPTION: SEQ ID NO:1:

ATGGCCCCCT TTGAGCCCCT G        2 1

( 2 ) INFORMATION FOR SEQ ID NO:2:

( i ) SEQUENCE CHARACTERISTICS:

(A) LENGTH: 18 base pairs
(B) TYPE: nucleic acid
(C) STRANDEDNESS: single
(D) TOPOLOGY: linear (ii) MOLECULE TYPE: other nucleic acid (iii) HYPOTHETICAL: NO (xi) SEQUENCE DESCRIPTION: SEQ ID NO:2:

CAGGATTCAG GCTATCTG 18

SERUM-FREE MEDIUM FOR TISSUE CULTURE CONTAINING TISSUE INHIBITOR OF METALLOPROTEINASES AND METHOD FOR GROWING CELLS USING THE MEDIUM

This application is a continuation of application Ser. No. 07/987,283 filed on Mar. 16, 1993, now abandoned.

TECHNICAL FIELD

The present invention relates to a TIMP (tissue inhibitor of metalloproteinases)-containing serum-free medium for culturing adherent cells or suspension cells, as well as to a method for growing adherent cells or suspension cells within a short period of time using the medium.

More particularly, the present invention relates to a TIMP-containing serum-free medium for tissue culture, which serves as a substitute for tissue culture media containing 10–15 % fetal calf serum (FCS), and also to a method for culturing, by using such serum-free medium, adherent or nonadherent cells isolated and established from mammals, suspension cells, e.g., human or mouse suspended fused cells, or the like.

BACKGROUND ART

Tissue inhibitor of metalloproteinases, hereinafter referred to as TIMP, a sialoglycoprotein having a molecular weight of about 30,000, is a specific inhibitor of the principal matrix metalloproteinases, i.e., interstitial collagenase, gelatinase/type IV collagenase (72 kDa and 92 kDa) and stromelysin. It, however, is known to have no inhibitory action on bacterial collagenase and thermolysin although they are likewise metalloenzymes (Cawston, In Proteinase Inhibitors (eds. Barrett A. J. and Salvesen G.) Elsevier, Amsterdam, pp. 589–610, 1986). TIMP is synthesized by a variety of cells, i.e., fibroblast cells, epithelial cells, endothelial cells, osteoblast cells, chondrocytes, platelets, macrophages and some tumor cells, and is also found in all kinds of mammalian body fluids (Welgus and Stricklin, J. Biol. Chem., 258, 12259–12264, 1983; Kodama et al., Matrix 9, 1–6, 1989). All this suggests that TIMP is a basic and universal protein in mammals.

Docherty et al. (Nature 318, 66–69, 1985) established the total amino acid sequence of TIMP on the basis of cDNA analysis. This sequence has been found to be identical in its entirety with the amino acid sequence of erythroid potentiating activity (EPA) produced by HTLV-II infected Mo T lymphoblasts (Gasson et al., Nature, 315, 768–771, 1985). EPA is also known to accelerate in vitro the growth of the human erythroblastic leukemia cell line K562 (Avalos et al., Blood, 71, 1720–1725, 1988). Recently, Hayakawa et al. (FEBS Lett., 268, 125–128, 1990) have demonstrated that TIMP produced by KM 102, a human bone marrow interstitial cell line, accelerates the colony formation of burst-forming units-erythroid (BFU-E) and colony-forming units-erythroid (CFU-E) cells. On the other hand, it has been demonstrated that the 22 kDa protein which is an expression product of 16C8, one of the "cell division cycle" genes of normal mouse fibroblast cells, is entirely identical with mouse TIMP (Gewert et al., EMBO J., 6, 651–657, 1987), and corresponds to human TIMP/EPA (Edwards et al., Nucleic Acid Res., 14, 8863–8878, 1986). These facts are suggestive of the possibility of TIMP being active as a cell growth factor not only for erythroid precursor (stem) cells but also for other cells.

The present inventors previously succeeded in the preparation of mouse monoclonal antibodies to bovine dental pulp TIMP, and found that antibodies from several out of these clones react specifically with TIMP present in human dental pulp tissue cultures (Kodama et al., Collagen Rel. Res. 7, 341–350, 1987). The present inventors also succeeded in determining with high sensitivity TIMP in the bovine or human body fluid or blood by sandwich enzyme immunoassay (EIA) using combinations of these antibodies (Kodama et al., Matrix 9, 1–6, 1989). It has been well known in the art that the addition of fetal calf serum (FCS) to tissue culture media results in acceleration of cell growth without exception, but it remains to be established what component (or components) in FCS acts (or act) as a growth factor.

The present inventors found the TIMP concentration in FCS to be about 250 ng/ml when measured by a sandwich EIA using the above mentioned monoclonal antibodies. The monoclonal antibodies were likewise used to prepare an affinity column for removal of TIMP from FCS, and a culture medium prepared from the thus obtained TIMP-free FCS was used to culture human gingival fibroblast cells. Such human gingival fibroblast cells cultured in TIMP-free FCS medium showed little growth up to day 3, and upon further addition to the culture medium of anti-TIMP monoclonal antibodies, no growth. On the other hand, when such culture was carried out in a culture medium prepared from TIMP-free FCS while adding purified TIMP thereto, it was found that the cell growth was commensurate with the concentration of TIMP added and, at a TIMP concentration of 100 ng/ml, the cell growth reached a level comparable to that as found in conventional 10% FCS-supplemented culture media.

It was also found that when adherent and nonadherent cells were cultured in serum-free medium supplemented with 100 ng/ml of TIMP a cell growth acceleration effect comparable to that as found with conventional 10% FCS-supplemented culture media was achieved.

On the basis of these findings, the present inventors have confirmed the effect of TIMP as a growth factor on cell growth, and succeeded in providing serum-free media extremely suitable for the culture of adherent and nonadherent cells by adding TIMP as a substitute for FCS to serum-free media.

DISCLOSURE OF INVENTION

According to the present invention, there is provided a serum-free medium for tissue culture characterized by containing TIMP, as well as a method for growing animal tissue cells or fused animal-derived cells characterized by culturing them in a serum-free tissue culture medium containing the TIMP as cell growth factor. As the TIMP to be added to the tissue culture media according to the present invention there may be used for purification products from tissues, blood, body fluids or macrophages of mammals or from normal or tumor cells isolated from mammals, it being also possible to use those TIMP products prepared by recombinant DNA methods as described in Japanese published unexamined patent application Nos. 61-282095 and 61-501640.

According to the present invention, there are provided novel media which can be used as substitutes for 10–15% FCS-containing tissue culture media, i.e., serum-free tissue culture media with certain amounts of TIMP/EPA added. There is also provided an extremely useful culture method for different cells such as adherent or nonadherent cells isolated and established from mammals or human or mouse suspended fused cells growing in such TIMP-containing serum-free media.

The present invention has made extremely great industrial contributions. Thus, for example, it can reduce the current high cost as incurred in using conventional fetal calf serum-containing culture media, and also can facilitate the purification of protein products contained in the culture media at low concentrations. The present invention also has the advantage that the recent criticism against the production of fetal calf sera in the growing movement of animal protection can be mitigated.

The present invention is further illustrated below by way of examples, although it is by no means limited to these examples.

TIMP to be used in the following examples was prepared in the following manner.

(a) Preparation of anti-TIMP monoclonal antibodies

In accordance with the procedure as described in Japanese published unexamined patent application No. 63-219392, mouse monoclonal antibodies to bovine dental pulp TIMP were prepared. Ascites fluids were taken from Balb/c mice to which had been administered fused cells from three out of the resultant seventeen clones, i.e., clone Nos. 7-6C1, 7-21B12 and 7-23G9. The monoclonal antibody in each of the thus obtained ascites fluids was purified in accordance with the procedure as described by Kodama et al. in Collagen Rel. Res., 7, 341–350, 1987.

(b) Preparation of FCS without TIMP

Removal of TIMP from FCS was carried out, in accordance with the procedure as described by Kodama et al. in J. Immunol. Meth., 127, 103–108, 1990, by passing the FCS through an anti-TIMP monoclonal antibody (clone No. 7-21B12)-Sepharose affinity column to remove TIMP from FCS. Subsequently, the passed through fractions were sterilized using a Falcon 7104 bottle top filter (0.45 μm, Becton Dickinson).

(c) Purification of TIMP

TIMP was purified from culture media conditioned by human gingival fibroblast cells (Gin-1 Cells) by chromatography on Ultrogel AcA44, Con A Sepharose and anti-TIMP monoclonal antibody-Sepharose affinity columns, followed by treatment in 4M guanidine-HCl at 35° C. for 30 minutes and then by chromatography on a Bio-Gel P60 column, for dissociation/fractionation to remove cell growth factors which may be binding to the TIMP.

(d) Determination of the TIMP concentration in FCS

The TIMP content was determined for fourteen FCS samples obtained from Biocell, Bockneck, BMA, Boehringer or Gibco in accordance with the method as described in Matrix 9, 1–6, 1989, to be 124–357 ng/ml (253±16 ng/ml, mean±SD).

EXAMPLE 1

(a) Studies on time course of Gin-1 cell growth

The time course of the growth of Gin-1 cells was studied under different culture conditions.

Figure 1:
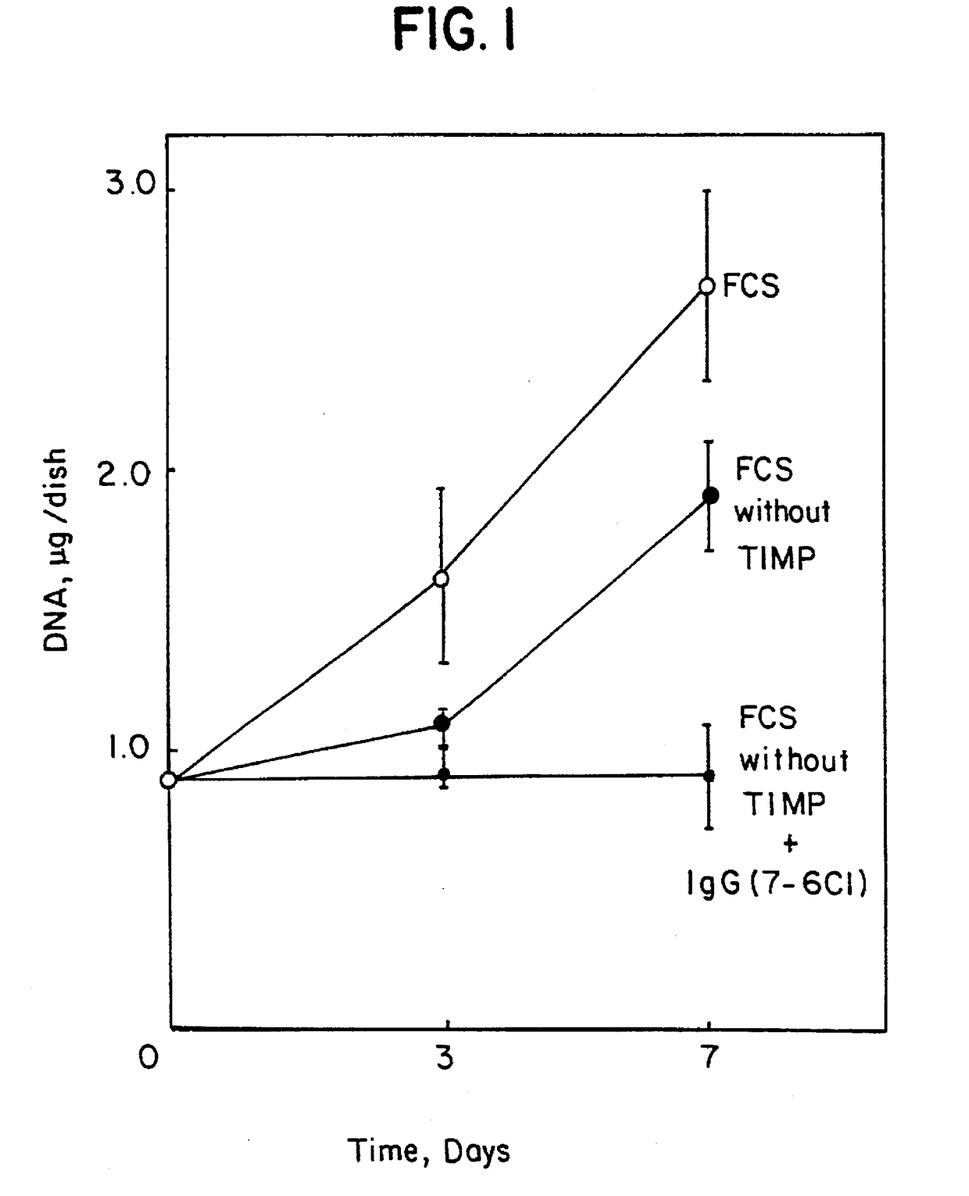
FIG. 1 is a graph showing time course of human Gin-1 cell growth under different conditions.

Thus, for example, the degree of Gin-1 cell growth was studied in accordance with the method as described by Hinegardner in Anal. Biochem., 39, 197–201, 1971, using the cellular DNA content as a measure thereof. The results are shown in. FIG. 1. As apparent from the figure, the Gin-1 cells showed an almost linear growth until they grew to confluence (seven days) when grown in conventional 10% FCS (-○-). They showed, however, little growth up to day 3 when grown in TIMP-free FCS (-●-) and some recovery of growth was observed thereafter, with the growth at day 7 reaching about 60% of that in the 10% FCS group. This recovery of growth was, however, completely inhibited by adding an anti-TIMP monoclonal antibody (clone No. 7-6C1, 54 ng/ml, -▲-) to the culture medium. The DNA contents are expressed here as the mean±S. D. of three dishes.

Figure 2:
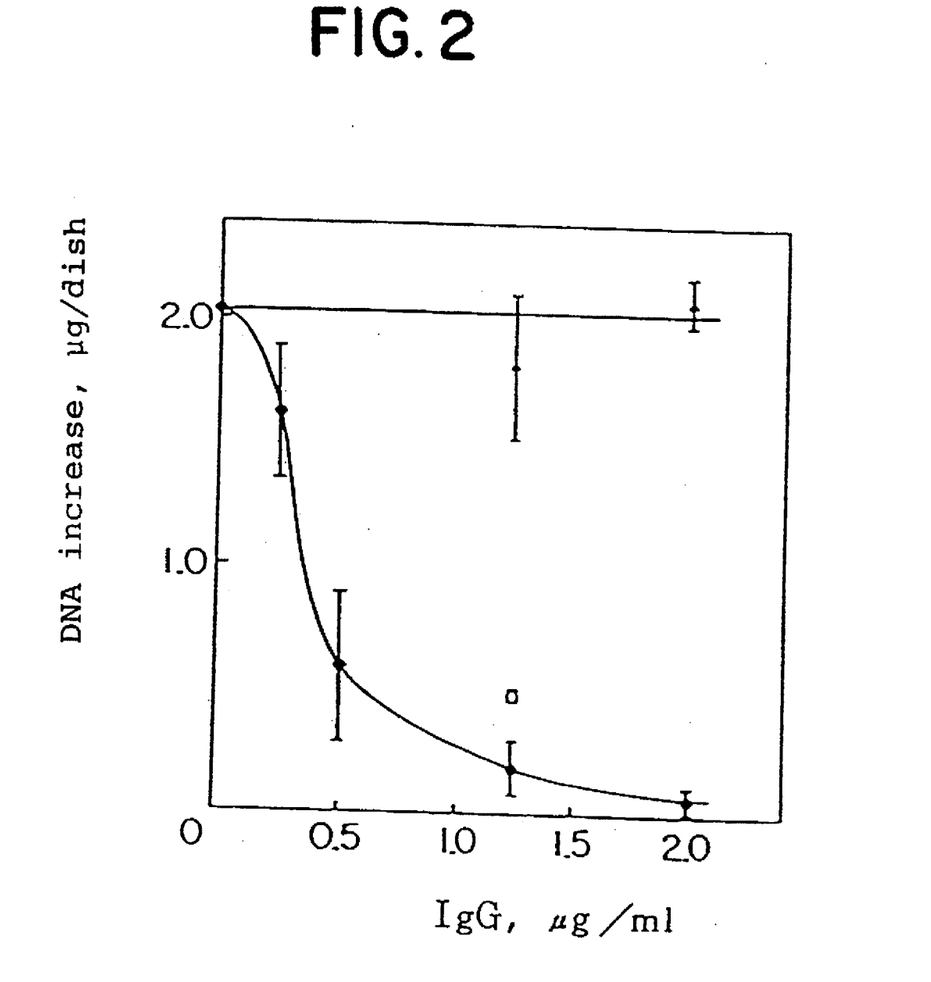
FIG. 2 is a graph showing the influence of anti-TIMP monoclonal antibodies on human Gin-1 cell growth.

To study the influence of anti-TIMP monoclonal antibodies on this Gin-1 cell growth, one of the anti-TIMP monoclonal antibodies (clone No. 7-6C1) was added to the culture medium of Gin-1 cells and the DNA content at day 7 was measured (-●-). As shown in FIG. 2, a significant growth inhibition was observed which was dependent on the amounts of the antibody added. Such growth inhibition was also observed with clone No. 7-23G9 (-○-), another antibody which recognizes a different epitope on the TIMP molecule. In contrast, there was observed no such inhibition with mouse immunoglobulin used as control (-▲-). The DNA content at day 0 was 0.891±0.018 μg/dish.

(b) Influence of TIMP concentrations on Gin-1 cell growth

Figure 3:
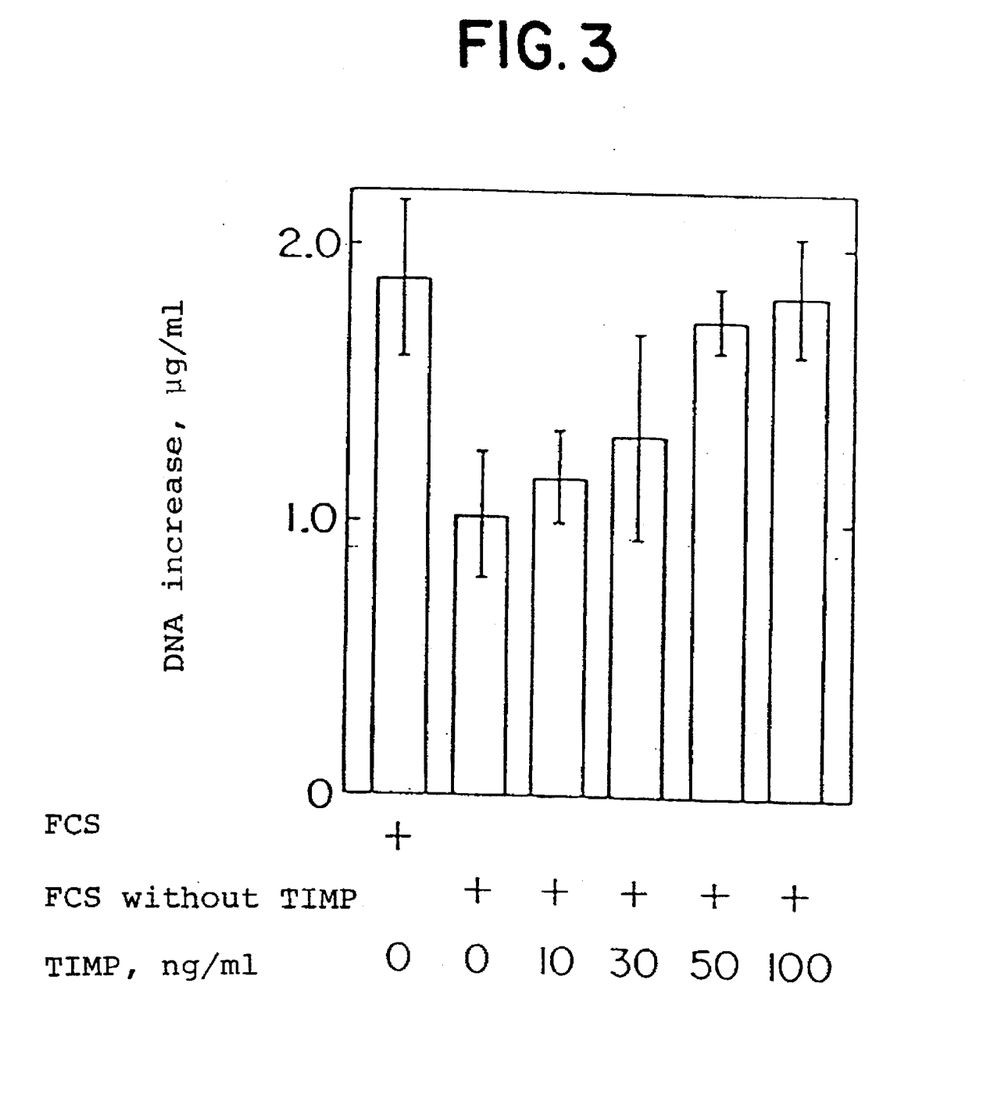
FIG. 3 is a graph showing the dependence of human Gin-1 cell growth on TIMP concentration.

The influence of varied concentrations of TIMP added to TIMP-free 10% FCS containing medium on Gin-1 cell growth was studied. As shown in FIG. 3, the DNA content depended on the TIMP concentrations during culturing for 7 days. The growth was fully restored by the addition of TIMP to the culture system at a concentration of 100 ng/ml as compared with control 10% FCS. The DNA content at day 0 was 0.891±0.018 μg/dish.

EXAMPLES 2–7

Effect of TIMP on the growth of different nonadherent cells

Figure 4:
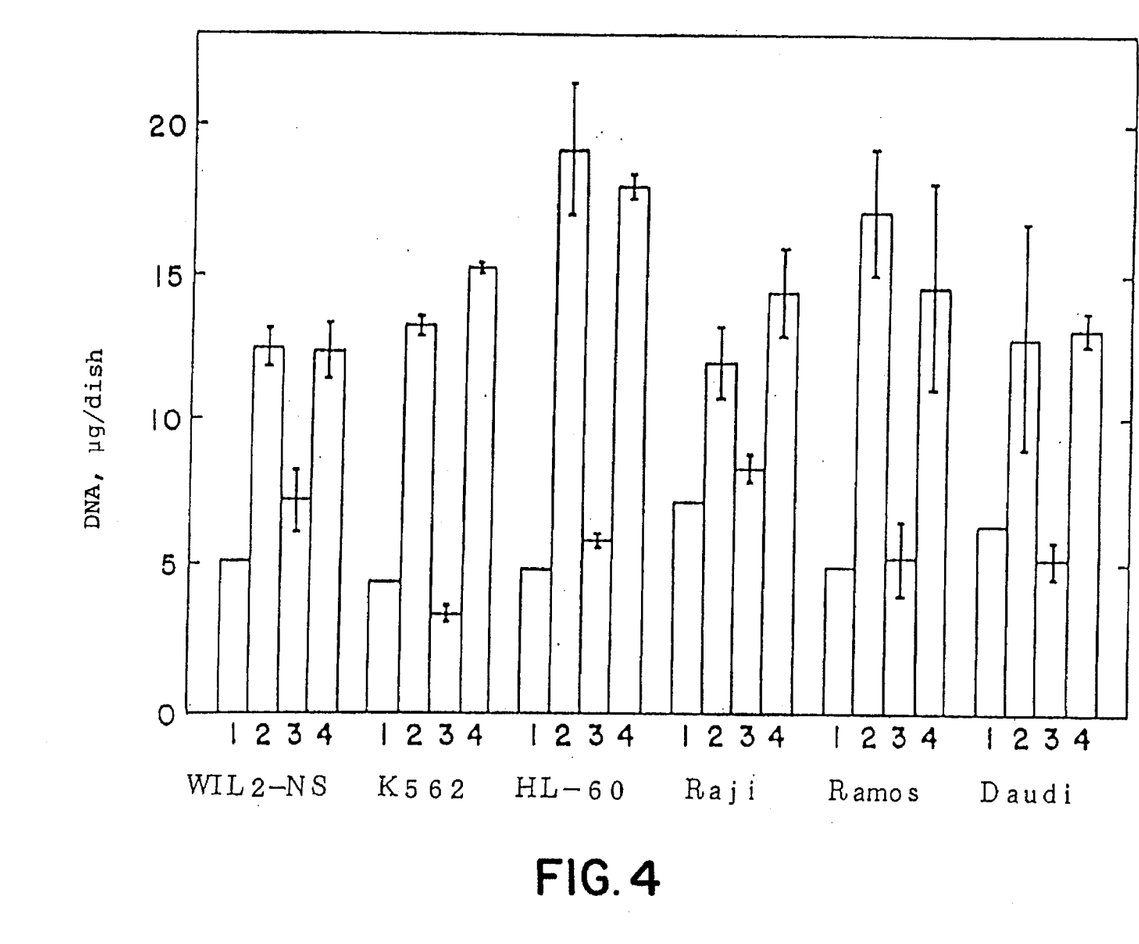
FIG. 4 is a graph showing the effect of TIMP on the growth of different nonadherent cells.
Figure 5A:
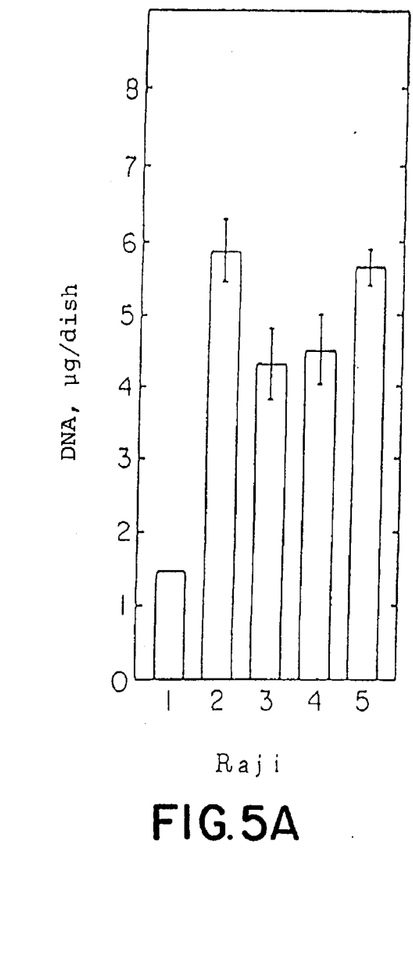
FIG. 5 is a graph showing the effect of TIMP addition on the growth of different cells in serum-free medium for tissue culture (ASF-104)
Figure 5B:
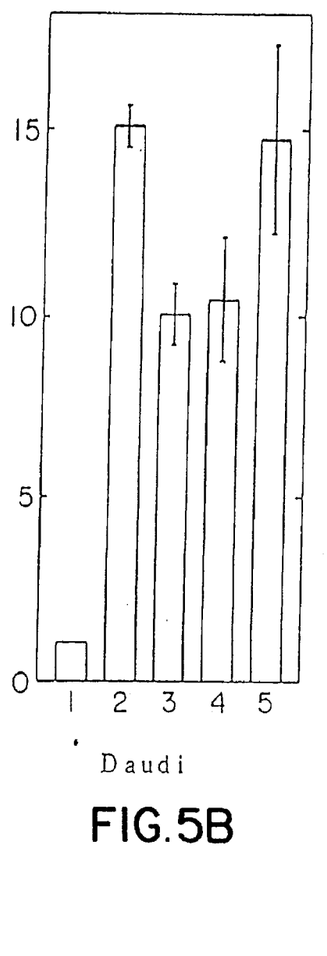
Figure 5C:
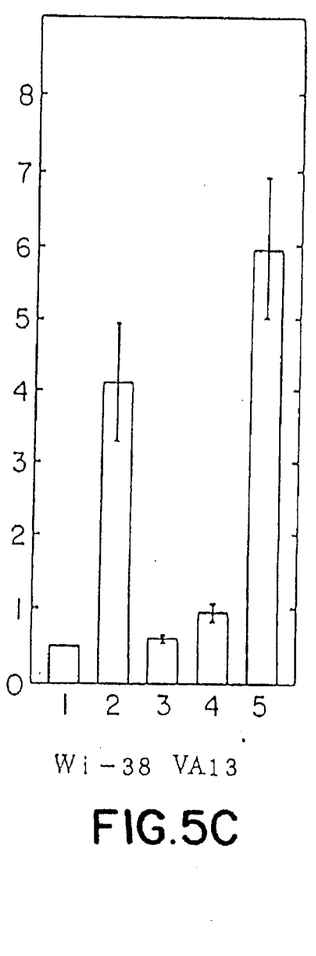
Figure 5D:
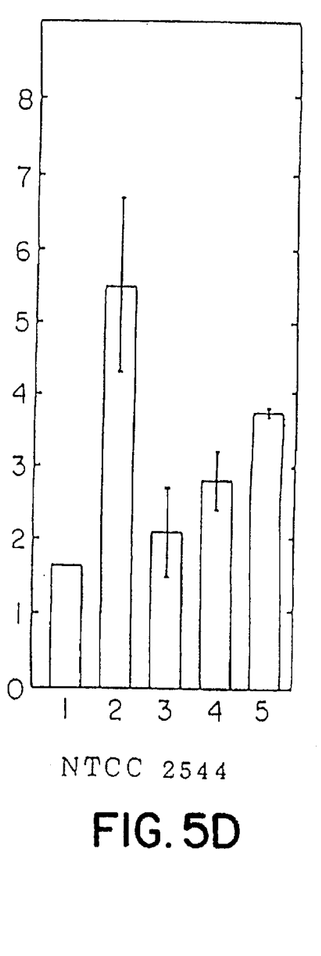

Whereas the Gin-1 cells used in Example 1 were adherent cells, nonadherent cells were used in Examples 2–7, i.e., human lymphoblast cells (non-secreting variant, WIL2-NS), human chronic erythroleukemia cells (K-562), human acute myclogenous leukemia cells (HL-60) and Burkitt lymphoma cells (Raji, Ramos and Daudi), respectively. The influence of TIMP on the growth of these nonadherent cells was studied, following the same procedure as in Example 1. The results are shown in FIG. 4 (1: at day 0; 2: 10% FCS; 3: 10% TIMP-free FCS; 4: 10% TIMP-free FCS+100 ng/ml TIMP). All of these cells showed little growth when cultured for two days in TIMP-free FCS (3), but an almost comparable growth to that observed in the control 10% FCS (2) when 100 ng/ml TIMP was added to the 10% TIMP-free FCS (4) (1: at day 0; 2,3 and 4: at day 2). There was thus observed no difference, with respect to the TIMP dependency of the cell growth, between adherent cells and nonadherent cells.

EXAMPLES 8–11

Effect of TIMP addition to serum-free media

Nonadherent cells (Raji and Daudi) and adherent cells (SV40-transformed human lung fibroblast cells (Wi-38 VA13) and human skin epithelial cells (NTCC 2544)) were used and tested in each case for determining the effect of TIMP addition on their growth in serum-free medium ASF-104 (Table 1). The results were expressed in terms of mean±S. D. obtained from three dishes at day 3 samples with Raji cells and Daudi cells and at day 7 samples with Wi-38 VA13 cells and NTCC 2544 cells. They are shown in FIG. 5. As is apparent from this figure (1: at day 0; 2: 10% FCS; 3: ASF-104; 4: ASF-104+30 ng/ml TIMP; 5: ASF-104+100 ng/ml TIMP), a significant cell growth acceleration effect, as well as a comparable cell growth to that observed with culture in 10% FCS (2), was observed for all of these cells at a TIMP concentration of 100 ng/ml (5 and Table 1). Exactly the same cell growth acceleration effect was observed with the other commercially available serum-free tissue culture media, i.e., Iscove's modified Dulbecco's medium and D-MEM/F-12 mixed medium, with 100 ng/ml TIMP added in each case as shown in Tables 2 and 3.

In the following will now be described the preparation of rTIMP and bnTIMP to be used in the examples below.

(a) Preparation of human recombinant TIMP (rTIMP)

(1) Extraction of cytoplasmic mRNA

After human Gin-1 cells were cultured in 10% FCS-containing D-MEM medium until just before confluence, the medium was replaced by D-MEM medium without FCS. Under such starvation, culture was continued for 24 hours to induce the biosynthesis and accumulation of mRNA coding for TIMP. The thus obtained cultured cells were washed with ice cold PBS on culture dishes and then scraped with a scraper under ice cooling. The scrapings were resuspended in a small amount of PBS and collected by centrifugation at 4° C. The cells were suspended in buffer for RNA extraction (0.14M NaCl, 15 mM $MgCl_2$, 10 mM Tris-HCl, pH 8.6, 0.5% Nonidet P-40, 1 mM DTT), lysed for five minutes under ice cooling and then centrifuged at 4° C. to recover the supernatant. To this supernatant, an equal volume of buffer for proteolytic enzymes at two-fold concentration (0.4M Tris-HCl, pH 8.0, 50 mM EDTA, 0.6 M NaCl, 4% SDS) was added, and Proteinase K was added to a final concentration of 50 µg/ml. The mixture was then allowed to stand at 37° C. for 30 minutes in order for proteolysis to proceed. There was thus obtained the cytoplasmic mRNA fraction.

(2) Selection of poly $A^+$ mRNA

Oligo(dT)-cellulose equilibrated with poly A loading buffer (20 mM Tris-HCl, pH 7.6, 0.5M NaCl, 1 mM EDTA, 0.1% Na-lauryl sarcosinate) was added directly to the cytoplasmic mRNA fraction obtained in (1) above, which had been warmed up to 65° C. and then rapidly quenched down to room temperature, with gentle stirring at room temperature. The mixture was poured into a silanized glass column to remove the supernatant. The oligo(dT)-cellulose was thoroughly washed with poly A loading buffer to elute and remove mRNAs without a poly A tail. The poly $A^+$mRNA adsorbed on the oligo(dT)-cellulose was eluted with buffer for poly $A^+$RNA elution (10 mM Tris-HCl, pH 7.8, 1 mM EDTA, 0.05% SDS), and the thus eluted RNA fractions were collected. One tenth the volume of sodium acetate buffer, pH 5.2, was added to the recovered poly $A^+$mRNA fraction and then two and a half volumes of ethanol were used to precipitate the poly $A^+$mRNA. The precipitate was washed with 70% ethanol, dried and then dissolved in distilled water.

(3) Synthesis of cDNA

The synthesis of the first strand cDNA was carried out with the poly $A^+$mRNA from (2) above used as the template for reverse transcription and oligo dT(12–18 mer) as the primer. The poly $A^+$mRNA was added to an ice cold solution for reaction with reverse transcriptase [50 mM Tris-HCl, pH 7.3, 75 mM KCl, 10 mM DTT, 3 mM $MgCl_2$, 0.5 mM dGTP, 0.5 mM dATP, 0.5 mM dTTP, 0.5 mM dCTP, 10 µg/ml oligo dT (12–18 mer)] at a concentration of 20 µg/ml and reverse transcriptase derived from Moloney murine leukemia virus was added. The reaction was carried out at 37° C. for one hour to obtain the hybrid double strand from the first strand cDNA and the mRNA.

(4) Design of PCR primer

From the cDNA sequence corresponding to TIMP (Docherty et al., Nature 318, 66–69, 1985), the following oligodeoxyribonucleotides complementary to the 5'- and 3'-ends of the TIMP gene were designed as PCR primers:

| | |
|---|---|
| Primer "TIMP-F1" with the nucleotide sequence 5'-ATG GCC CCC TTT GAG CCC CTG-3'; | SEQ ID NO: 1 |
| Primer "TIMP-R1" with the nucleotide sequence 5'-CAG GAT TCA GGC TAT CTG-3'. | SEQ ID NO: 2 |

(5) Synthesis of primers

The primers were synthesized by the β-amidide method using a MilliGen/Biosearch DNA synthesizer (Cyclone) in accordance with the instructions by the manufacturer. The oligonucleotides thus obtained were precipitated with ethanol, washed with 70% ethanol, dried and dissolved in distilled water.

(6) Specific amplification of TIMP cDNA by PCR

A PCR reaction system was prepared by using as the template the first strand cDNA and the mRNA hybrid double strand prepared as described above, and as the primer for duplication, the two oligodeoxyribonucleotides TIMP-F1 and TIMP-R1 prepared as described above. Thus, 300 ng each of the primers TIMP-F1 and TIMP-R1 and 1 µl of the hybrid double strand from the first strand cDNA and the mRNA were added to a PCR reaction cocktail (67 mM Tris-HCl, pH 8.8, 16.6 mM $(NH_4)_2SO_4$, 1.5 mM $MgCl_2$, 10 mM β-mercaptoethanol, 6.7 µM EDTA, 170 µg/ml BSA, 0.2 mM dGTP, 0.2 mM dATP, 0.2 mM dTTP, 0.2 mM dCTP). After addition of Taq polymerase, the amplification cycle of heating at 93° C. for 2 minutes, at 48° C. for 1.5 minutes and then at 65° C. for 1.5 minutes was repeated 30 times. The thus obtained PCR product was found by agarose gel electrophoresis to be a DNA fragment of about 630 base pair length.

(7) Subcloning of amplified DNA fragment

The DNA fragment of about 630 base pair length, i.e., the PCR product defined by the primers TIMP-F1 and TIMP-R1, was excised from the gel after agarose gel electrophoresis and then purified. The thus purified, about 630 base pair DNA fragment was directly linked to the restriction enzyme SmaI site of plasmid pUC 13 to give plasmid pUFYK-1. The pUFYK-1 was cleaved with the restriction enzymes BamHI and EcorI and the so defined DNA fragment was linked to the restriction enzyme BamHI and EcoRI site of pIC-20H (Marsh et al., Gene 32, 481–485, 1984) to give plasmid pFYK-2.

(8) Construction of vector for TIMP gene expression in *Escherichia coli*

The pFYK-2 was cleaved with the restriction enzymes BamHI and XhoI and then subjected to agarose gel electrophoresis. An about 630 base pair DNA fragment was excised from the gel and purified. The purified, about 630 base pair DNA fragment was linked to the restriction enzyme BamHI and SalI site of plasmid pEX (Stanley et al., EMBO J. 3, 1429–1434, 1984) to give plasmid pFEX4.

(9) Introduction into and expression in *Escherichia coli* of TIMP gene

The pFEX4 was used to transform the *Escherichia coli* strain NF1 (ATCC 33767) and the strain harboring pFEX4 was selected. The thus transformed strain was inoculated into LB medium containing 50 µg/ml ampicillin and subjected to culture with vigorous shaking overnight at 30° C. The resultant culture was inoculated again into LB medium containing 50 µg/ml ampicillin and subjected to culture with shaking for 2.5 hours at 30° C. Then the temperature was shifted to 42° C. and the culture was shaken for a further 1.5 hours. The culture was chilled in ice and the cells were harvested by centrifugation, suspended directly in sample buffer for SDS-PAGE, heat-treated and then subjected to SDS-PAGE for analysis of all proteins derived from the pFEX4-transformed *Escherichia coli* strain. When analyzed by the Western blotting method using mouse anti-TIMP monoclonal antibodies, proteins accumulated in the cells concomitantly with the induction of the lac Z gene expression of pFEX4 were TIMP positive. The pFEX4 was thus confirmed to contain TIMP gene.

(10) Construction of vector for TIMP gene expression in CHO cells

The pFYK-2 was cleaved with the restriction enzymes SalI and XhoI, and subjected to agarose gel electrophoresis, whereafter an about 630 base pair DNA fragment was excised from the gel and purified. The purified, about 630 base pair DNA fragment was cleaved with the restriction enzyme SalI and then linked to plasmid pMAM-neo (Lee et al., Nature 294, 228–232, 1981) dephosphorylated with alkaline phosphatase to give plasmid pMAMPT1.

(11) Gene introduction into cultured cells

CHO (Chinese hamster ovary) cells were used as host cells to introduce gene. The introduction was carried out by the conventional calcium phosphate coprecipitation procedure. CHO cells were cultured in 10% FCS-containing HamF12 medium using a 25cm$^2$ culture flask so that their growth reached 80–90% confluency on the day of DNA introduction. About 10 μg of purified pMAMPT1 DNA was added to a mixture of 250 μl of 2xHBS (Hank's balanced salts; 1.4 mM $Na_2HPO_4$, 10 mM KCl, 12 mM glucose, 275 mM NaCl-containing 40 mM HEPES, pH 6.95) and 30 μl of 2M $CaCl_2$ and the mixture was made up to 500 μl with TE buffer (1 mM EDTA-containing 10 mM Tris-HCl, pH 8.0). The mixture was allowed to stand at room temperature for 30 minutes for DNA-calcium phosphate precipitation. The medium was removed from the cultured cells and 3.5 ml/25 cm$^2$ culture flask of fresh medium was added; afterwards the DNA-calcium phosphate suspension was added into the medium. The system was incubated at 37° C. for 4 hours. The DNA-calcium phosphate precipitate was discarded together with the medium, and the cells were washed with 2.5 ml/25 cm$^2$ culture flask of FCS-free HamF12 medium. 1 ml/25 cm$^2$ culture flask of 10% DMSO solution was added and the mixture was allowed to stand at room temperature for 2–4 minutes, whereafter the DMSO was removed. 1.7 ml/25 cm$^2$ culture flask of HamF12 medium containing 10% FCS and 0.1 mM chloroquine was added and the mixture was incubated at 37° C. for 2.5 hours, whereafter the added chloroquine was removed. The cells were washed with FCS-free HamF12 medium and, after the addition of 10% FCS-containing HamF12 medium, cultured for 2 days. They were further cultured in HamF12 selection medium containing 500 μg/ml geneticin (G418) and 10% FCS for selection of transfected cells.

(12) Expression in cultured cells and purification of gene

The transfected cells were inoculated into a suspension of Cytodex 2 microcarrier (Pharmacia) in 10% FCS-containing ASF-104 serum-free medium. The FCS concentration was lowered gradually down to 0% over a period of 4–5 days. The cells were subsequently cultured in FCS-free ASF-104 serum-free medium for about 10 days, while carrying out induction with dexamethasone. The supernatant of the resultant culture was recovered for purification of rTIMP. The supernatant at that point in time was found to contain about 2 μg/ml of rTIMP.

The recovered supernatant was applied on a mouse anti-human TIMP monoclonal antibody-bound Sepharose 4B affinity column and eluates after washing were subjected to gel filtration on an Ultrogel AcA54 column. rTIMP-containing fractions were then further concentrated.

(13) Properties of rTIMP expressed in cultured cells

The thus purified rTIMP showed a single band of about 30 KDa in SDS-PAGE (12.5% homogeneous gel; reducing conditions).

A single band of about 30 kDa was also shown in Western blotting (staining with peroxidase-labeled mouse anti-human TIMP monoclonal antibodies).

The inhibitory activity of rTIMP on collagenase derived from CCD-41SK cells was determined to be about $1\times10^{-9}$M in terms of $IC_{50}$.

(b) Preparation of bovine dental pulp TIMP (bnTIMP)

bnTIMP was purified from culture media conditioned by bovine dental pulp tissues in accordance with the procedure as described by Kodama et al. in Collagen Rel. Res., 7, 341–350, 1987.

EXAMPLE 12

Effect of rTIMP on Gin-1 cell growth

Figure 6:
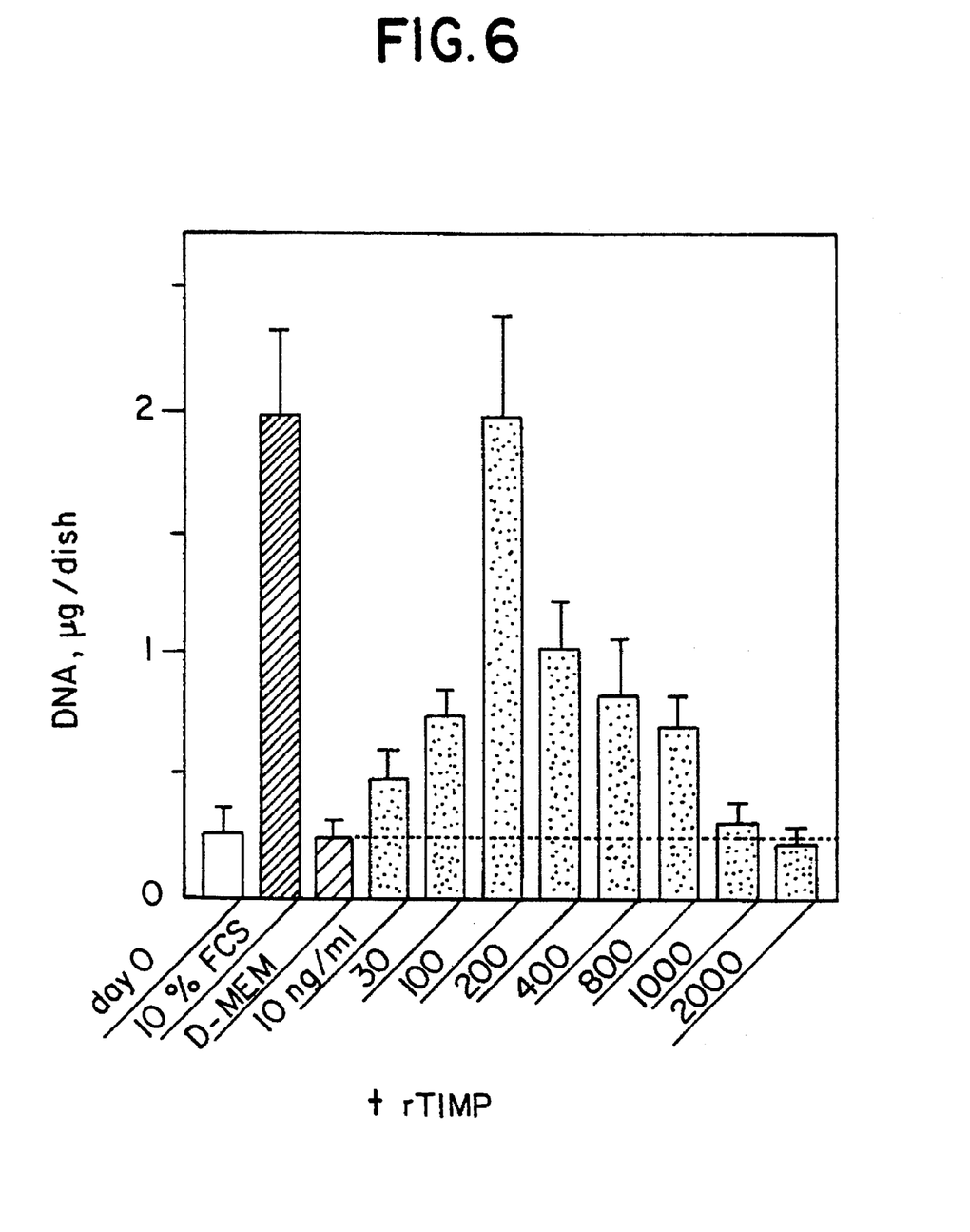
FIG. 6 is a graph showing the effect of human rTIMP addition on the growth of human Gin-1 cells in D-MEM serum-free medium.

The effect of rTIMP concentrations on the growth of human Gin-1 cells was studied as described above in Example 1 (b). As shown in FIG. 6, almost 100% growth, as compared with the growth in the 10% FCS-added group as the control, was found to be reached at a rTIMP concentration of 100 ng/ml.

EXAMPLE 13

Effect of rTIMP on K-562 cell growth

Figure 7:
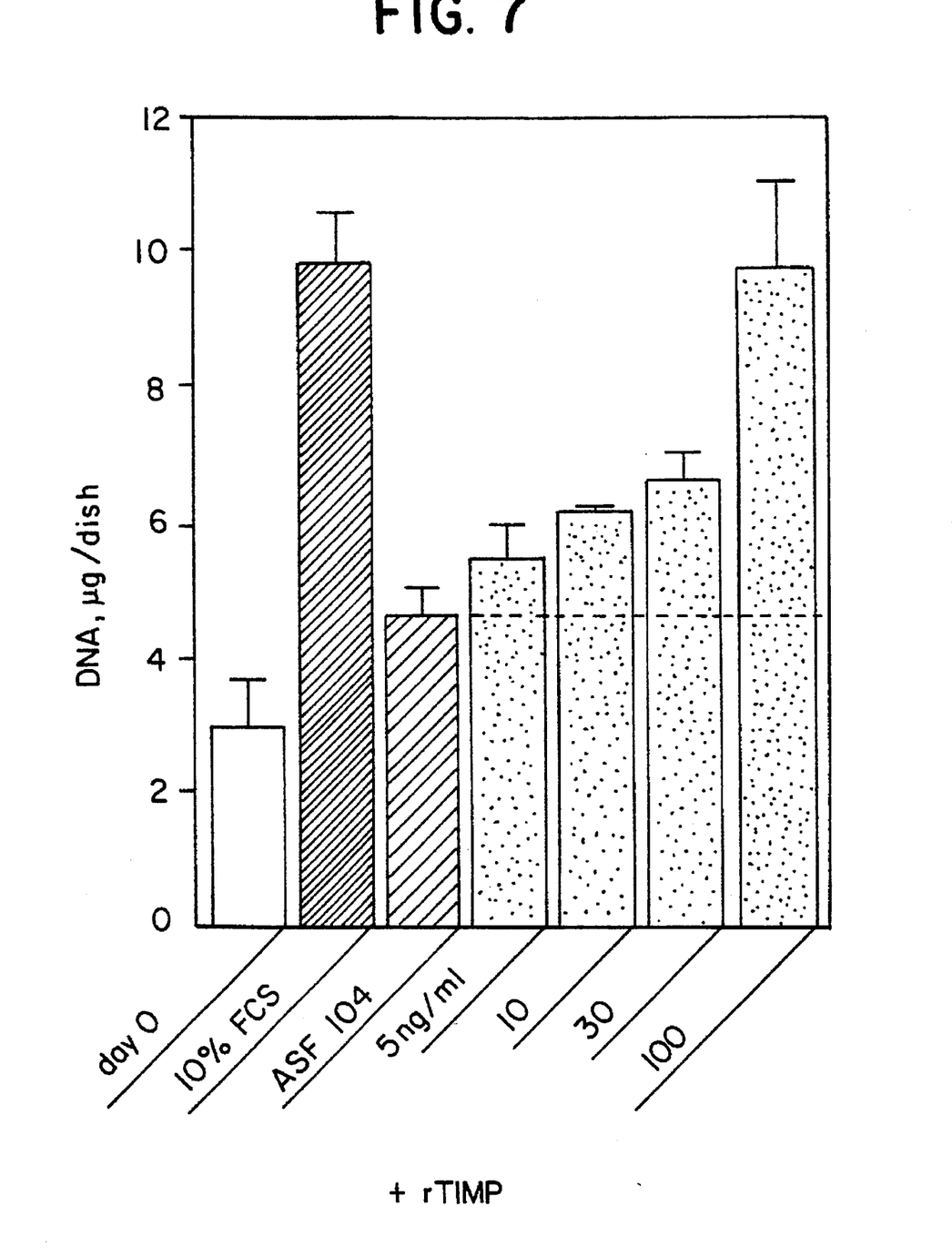
FIG. 7 is a graph showing the effect of rTIMP addition on the growth of human K-562 cells in ASF-104 serum-free medium.

The effect of rTIMP concentrations on the growth of human K-562 nonadherent cells was studied as described above in Examples 2–7. As shown in FIG. 7, almost 100% growth, as compared with the growth in the 10% FCS-added group as the control, was found to be reached at a rTIMP concentration of 100 ng/ml.

EXAMPLES 14 and 15

Effect of rTIMP or bnTIMP on mouse-derived colon 26 and 3T3 cell growth

Figure 8A:
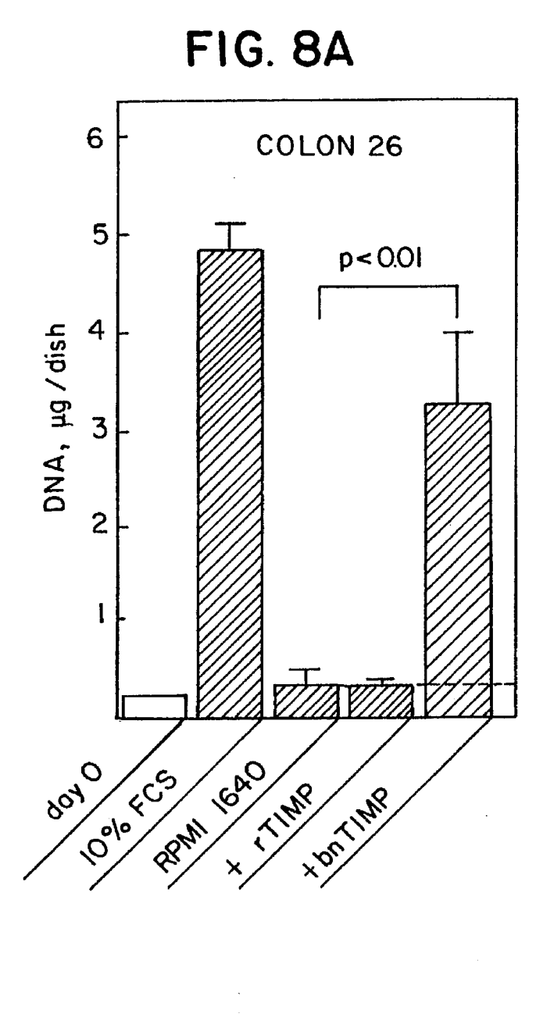
FIG. 8 is a graph showing the effect of human rTIMP or bnTIMP addition on the growth of mouse colon 26 cells in RPMI 1640 medium as well as on that of mouse 3T3 cells in D-MEM serum-free medium.
Figure 8B:
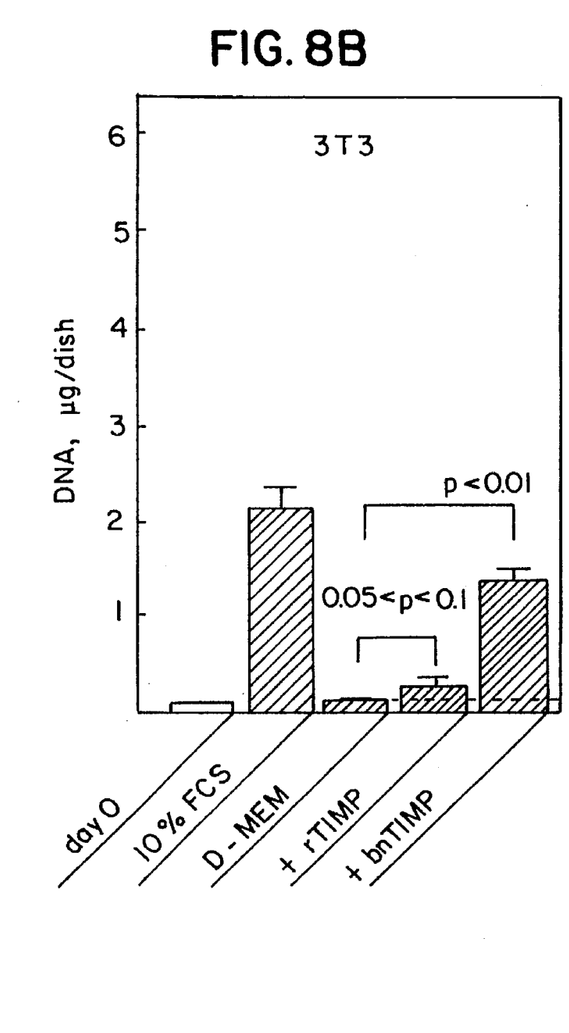

The effect of the addition of rTIMP or bnTIMP (each at 100 ng/ml) on the growth of mouse colon 26 cells (mouse rectum cancer colon 26 cells) was studied. As shown in FIG. 8, during the seven day culture, little growth was observed with the addition of rTIMP in RPMI 1640 medium but growth recovery up to 70%, as compared with the growth in the 10% FCS-added control group, with the addition of bnTIMP. Similar results were also observed with mouse 3T3 cells (3T3 Swiss albino cells—fetal mouse fibroblast cells).

EXAMPLE 16

Effect of rTIMP or bnTIMP on mouse-derived hybridoma growth

Figure 9:
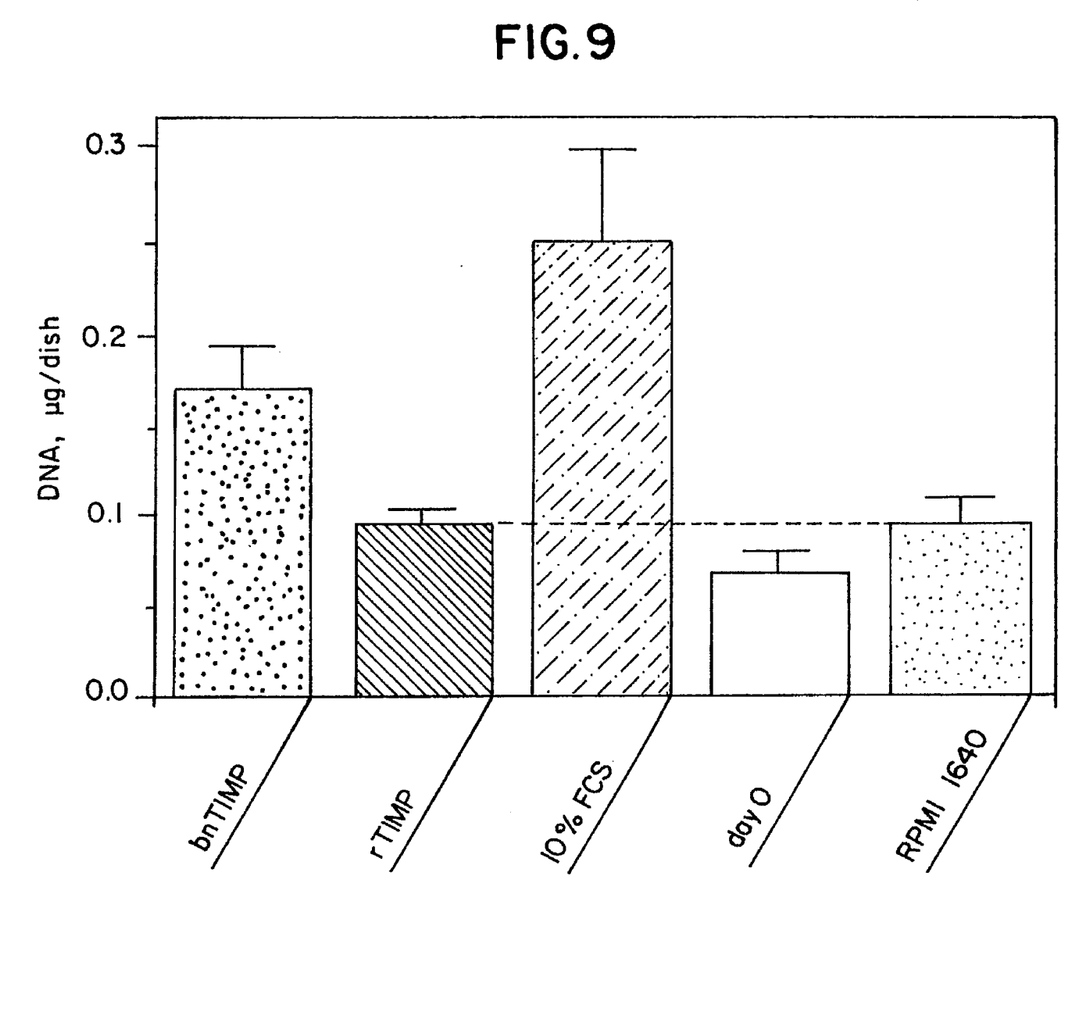
FIG. 9 is a graph showing the effect of bnTIMP or human rTIMP on the growth of mouse hybridoma, FGRM P-12200 in RPMI 1640 medium.

The effect of rTIMP or bnTIMP (each at 100 ng/ml) on the growth of mouse anti-human laminin monoclonal antibody-producing hybridoma (clone No. 22 - 3B10: deposited as FERM P-12200 with Fermentation Research Institute, Agency of Industrial Science and Culture, Ministry of International Trade and Industry, 1-1-3, Higashi, Tsukuba-shi, Ibaragi-ken, Japan) was studied. As shown in FIG. 9, no effect was observed with rTIMP, but growth recovery up to 70%, as compared with the growth in the 10% FCS-added group as the control, occurred with bnTIMP.

As is apparent from the experimental results mentioned above, TIMP in FCS has a distinguished growth acceleration effect on a wide variety of cells. Quite a few polypeptide hormones and growth factors have previously been discovered and demonstrated to accelerate the growth of cultured cells (Hayashi and Sato, Nature, 259, 132–134, 1976). Furthermore, a special cell line has also been established which can be subcultured even in media containing no proteinaceous factors (Okabe et al., Cancer Res., 46, 1043–1046, 1986). In general, most vertebrates require blood for their growth. This fact is suggestive of one or more unknown growth factors being contained in the blood. The growth acceleration activity of TIMP as demonstrated in accordance with the present invention suggests that TIMP is one of such unknown growth factors. Thus, the present invention has made it possible, by adding native TIMP or recombinant TIMP to synthetic artificial media, to carry out, at the same level as in FCS—containing media, such cell growth that has hitherto been supposed to be difficult or limited in synthetic artificial media of conventional type, which is a great contribution to the progress in different areas, such as cell culture researches and industrial applications.

TABLE 1

1) ASF104 medium
Composition in 1 liter

| | |
|---|---|
| L-alanine | 20.0 mg |
| L-arginine hydrochloride | 200.0 |
| L-asparagine (monohydrate) | 56.0 |
| L-aspartic acid | 20.0 |
| Sodium L-glutamate | 20.0 |
| L-cysteine hydrochloride (monohydrate) | 70.0 |
| Glycine | 30.0 |
| L-histidine hydrochloride (monohydrate) | 42.0 |
| L-isoleucine | 105.0 |
| L-leucine | 105.0 |
| L-lysine hydrochloride | 146.0 |
| L-methionine | 30.0 |
| L-phenylalanine | 67.0 |
| L-proline | 20.0 |
| L-serine | 80.0 |
| L-threonine | 95.0 |
| L-tryptophan | 25.0 |
| L-tyrosine | 64.0 |
| L-valine | 94.0 |
| L-ornithine hydrochloride | 100.0 |
| Glycyl L-glutamine | 500.0 |
| Alanyl L-glutamine | 500.0 |
| Glutathione (reduced form) | 1.0 mg |
| Biotin | 0.2 |
| Calcium D-pantothenate | 4.0 |
| Choline bitartrate | 20.0 |
| Folic acid | 4.0 |
| i-Inositol | 20.0 |
| Nicotinamide | 4.0 |
| Pyridoxal hydrochloride | 4.0 |
| Riboflavin | 0.4 |
| Thiamine hydrochloride | 4.0 |
| Vitamin $B_{12}$ | 0.1 |
| Calcium folinate | 0.01 |
| Disodium hypoxanthine | 2.0 |
| Sodium chloride | 8,000.0 |
| Potassium chloride | 400.0 |
| Calcium chloride | 100.0 |
| Magnesium sulfate | 98.0 |
| Zinc sulfate (heptahydrate) | 0.01 |
| Copper sulfate (pentahydrate) | 0.001 |
| Ferric nitrate (enneahydrate) | 0.1 |
| Sodium selenite | 0.004 |
| Sodium dihydrogenphosphate | 125.0 |
| Sodium hydrogencarbonate | 1,800.0 |
| HEPES | 1,200.0 mg |
| Sodium pyruvate | 220.0 |
| Succinic acid | 106.0 |
| Sodium succinate (hexahydrate) | 27.0 |
| Disodium β-glycerophosphate | 1,500.0 |
| Sodium ascorbate | 5.0 |
| Phenol Red (for culture medium) | 5.0 |
| Deoxyadenosine | 1.0 |
| Deoxycytidine | 0.03 |
| 6,8-Dihydroxypurine | 0.3 |
| Thymidine | 0.2 |
| Uridine | 5.0 |
| Putrescine dihydrochloride | 0.3 |
| Phosphoethanolamine | 28.0 |

TABLE 1-continued

1) ASF104 medium
Composition in 1 liter

| | |
|---|---|
| Cholesterol | 0.1 |
| Glucose | 2,000.0 |
| Mannose | 500.0 |
| Galactose | 200.0 |
| α-Cyclodextrin | 2,200.0 |
| α-Cyclodextrin-linoleic acid | 10.0 |
| Human transferrin | 5.0 |
| Crystalline insulin | 5.0 |
| Kanamycin | 60.0 |
| TIMP | 0.1 |

TABLE 2

2) Iscove's medium
Composition in 1 liter

| | |
|---|---|
| L-alanine | 25.0 mg |
| L-arginine hydrochloride | 84.0 |
| L-asparagine | 28.4 |
| L-aspartic acid | 30.0 |
| L-glutamic acid | 75.0 |
| L-glutamine | 584.0 |
| Disodium L-cystine | 82.8 |
| Glycine | 30.0 |
| L-histidine hydrochloride (monohydrate) | 42.0 |
| L-isoleucine | 105.0 |
| L-leucine | 105.0 |
| L-lysine hydrochloride | 146.0 |
| L-methionine | 30.0 |
| L-phenylalanine | 66.0 |
| L-proline | 40.0 |
| L-serine | 42.0 |
| L-threonine | 95.0 |
| L-tryptophan | 16.0 |
| Disodium L-tyrosine | 104.2 |
| L-valine | 94.0 |
| Biotin | 0.013 |
| Calcium D-pantothenate | 4.0 |
| Choline chloride | 4.0 mg |
| Folic acid | 4.0 |
| i-Inositol | 7.2 |
| Nicotinamide | 4.0 |
| Pyridoxal hydrochloride | 4.0 |
| Riboflavin | 0.4 |
| Thiamine hydrochloride | 4.0 |
| Vitamin $B_{12}$ | 0.013 |
| Potassium chloride | 330.0 |
| Potassium nitrate | 0.076 |
| Magnesium sulfate (heptahydrate) | 200.0 |
| Sodium chloride | 4,505.0 |
| Sodium dihydrogenphosphate (dihydrate) | 141.3 |
| HEPES | 5,962.0 |
| Calcium chloride (dihydrate) | 218.6 |
| Sodium Phenol Red | 15.0 |
| Sodium pyruvate | 110.0 |
| Sodium selenite | 0.017 |
| Sodium hydrogencarbonate | 2,520.0 |
| D-glucose | 4,500.0 |
| Bovine serum albumin | 400.0 |
| Human transferrin | 1.0 |
| Soybean lectin | 100.0 |
| TIMP | 0.1 |

TABLE 3

3) D-MEM/F-12 mixed medium
Composition in 1 liter

| | |
|---|---|
| L-alanine | 4.5 mg |
| L-arginine hydrochloride | 147.4 |
| L-asparagine (monohydrate) | 7.5 |

TABLE 3-continued

| 3) D-MEM/F-12 mixed medium Composition in 1 liter | |
|---|---|
| L-aspartic acid | 6.7 |
| L-cysteine hydrochloride (monohydrate) | 17.6 |
| L-cystine | 24.0 |
| L-glutamine | 365.1 |
| L-glutamic acid | 7.4 |
| Glycine | 18.8 |
| L-histidine hydrochloride (monohydrate) | 31.5 |
| L-isoleucine | 54.4 |
| L-leucine | 59.0 |
| L-lysine hydrochloride | 91.4 |
| L-methionine | 17.2 |
| L-phenylalanine | 35.5 |
| L-proline | 17.3 |
| L-serine | 26.3 |
| L-threonine | 53.6 |
| L-tryptophan | 9.0 |
| L-tyrosine | 38.7 |
| L-valine | 52.7 |
| Putrescine hydrochloride | 0.081 |
| Biotin | 0.004 mg |
| Calcium D-pantothenate | 2.1 |
| Choline chloride | 9.0 |
| Folic acid | 2.7 |
| i-Inositol | 12.5 |
| Nicotinamide | 2.0 |
| Pyridoxal hydrochloride | 2.0 |
| Pyridoxine hydrochloride | 0.031 |
| Riboflavin | 0.219 |
| Thiamine hydrochloride | 2.2 |
| Vitamin $B_{12}$ | 0.680 |
| D-glucose | 3,151.0 |
| Sodium pyruvate | 110.0 |
| Lipoic acid | 0.103 |
| Methyl linolenate | 0.044 |
| Copper sulfate | 0.001 |
| Ferric sulfate (heptahydrate) | 0.417 |
| Magnesium sulfate | 85.0 |
| Zinc sulfate (heptahydrate) | 0.432 |
| Ferric sulfate (enneahydrate) | 0.050 |
| Calcium chloride (dihydrate) | 154.5 |
| Potassium chloride | 311.9 |
| Sodium chloride | 7,000.0 |
| Sodium dihydrogenphosphate (dihydrate) | 62.5 mg |
| Sodium monohydrogenphosphate | 71.0 |
| Sodium hydrogencarbonate | 1,200.0 |
| Hypoxanthine | 2.0 |
| Thymidine | 0.364 |
| Sodium Phenol Red | 8.1 |
| TIMP | 0.1 |

We claim:

1. A method for growing established mammalian cells or isolated, fused mammalian cells in fetal calf serum-free growth medium comprising culturing said established mammalian cells or said isolated, fused mammalian cells in a fetal calf serum-free growth medium containing 10 to 800 ng/ml tissue inhibitor of metalloproteinases as a substitute for fetal calf serum, wherein said cultured cells do not differentiate.

2. The method of claim 1, wherein said established mammalian cells or said isolated, fused mammalian cells are adherent cells or non-adherent cells.

3. The method of claim 2, wherein said adherent cells are selected form the group consisting of human gingival fibroblast cells, SV40-transformed human lung fibroblast cells, and human skin epithelial cells.

4. The method of claim 2, wherein said non-adherent cells are selected from the group consisting of human lymphoblast cells, human chronic erythroleukemia cells, human acute myclogenous leukemia cells, and Burkitt lymphoma cells.

5. The method of claim 1, wherein said isolated, fused mammalian cells are fused human cells or fused mouse cells.

6. The method of claim 1, wherein said isloated, fused mammalian cells are hybridomas.

* * * * *